United States Patent [19]

Marsili et al.

[11] 4,124,585

[45] Nov. 7, 1978

[54] RIFAMYCIN COMPOUNDS

[75] Inventors: Leonardo Marsili; Vittorio Rossetti; Carmine Pasqualucci, all of Milan, Italy

[73] Assignee: Archifar Laboratori Chimico Farmacologici S.p.A., Rovereto, Italy

[21] Appl. No.: 738,352

[22] Filed: Nov. 3, 1976

[30] Foreign Application Priority Data

Nov. 12, 1975 [IT] Italy .................................. 5240 A/75

[51] Int. Cl.$^2$ ........................................... C07D 498/08
[52] U.S. Cl. .............................. 260/239.3 P; 424/244; 424/275; 424/274; 424/269; 424/285
[58] Field of Search .................................. 260/239.3 P

[56] References Cited

PUBLICATIONS

Kump et al., "Helv Chim. Acta" vol. 56, No. 7, (1973), pp. 2348–2377.
March "Advanced organic Chemistry" (McGraw–Hill), p. 667.

*Primary Examiner*—Natalie Trousof
*Assistant Examiner*—Robert T. Bond
*Attorney, Agent, or Firm*—Max Fogiel

[57] ABSTRACT

Novel rifamycin compounds having high antibiotic activity. Such compounds are obtained by reacting 3-amino-rifamycin SV with an aldehyde, particularly a heterocyclic aldehyde.

1 Claim, No Drawings

RIFAMYCIN COMPOUNDS

This invention relates to novel rifamycin compounds having high antibiotic activity.

In the DOS patent application No. 2.548.148 in the name of the same applicants a method is disclosed for providing 3-amino-rifamycin S having the following formula

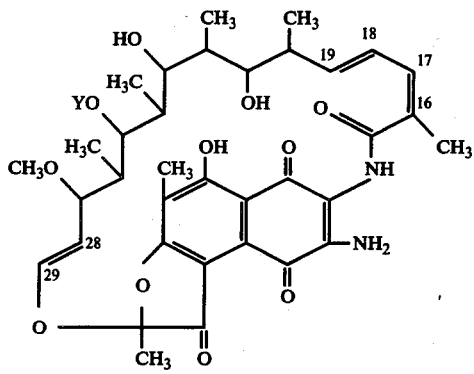

(III)

wherein Y is —COCH$_3$, and its 16, 17, 18, 19 tetrahydroderivative and its 16, 17, 18, 19, 28, 29 hexahydroderivative: such compounds show antibiotic characteristics.

Said compounds have been claimed in the German Pat. No. 1.670.377.

It is well known that rifamycin compounds can provide the respective 16, 17, 18, 19 tetrahydroderivatives and 16, 17, 18, 19, 28, 29 hexahydroderivatives having characteristics comparable to those of the starting compounds: the method for obtaining such derivatives would be apparent to those skilled in the art and is disclosed, for example, in the above mentioned German Pat. No. 1.670.377 and in Experientia 20, 336, (1964).

The compounds according to the present invention have the following formula

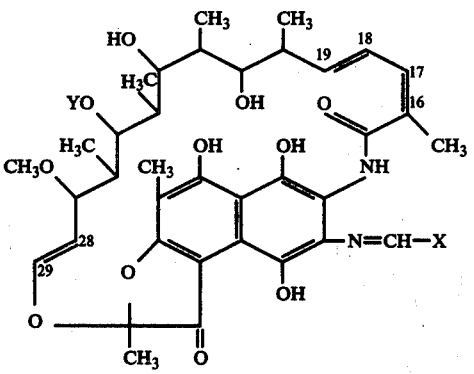

(I)

wherein: X is a radical selected from the group comprising aryl with less than 9 C atoms; arylalkenyl with less than 9 C atoms; a 5 and 6 member heterocyclo containing less than 5 heteroatoms selected from the group comprising N, O and S; a condensed 5 and 6 member heterocyclo with an aromatic ring, wherein the heterocyclo has less than 3 heteroatoms selected from the group comprising O and S; substitution products of the above specified radicals with at least one radical differing therefrom and selected from the group comprising in addition to all of the hereinabove specified radicals halogen, oxydryl, alkoxyl with less than 7 C atoms, nitro, amino, N-alkylamino with less than 3 C atoms, N,N-dialkylamino with less than 5 C atoms, carboxyl, carbalkoxy with less than 6 C atoms, carboxyalkoxy with less than 4 C atoms, N,N-dialkylaminoalkoxy with less than 7 C atoms, acetoxy, acetamido; Y is —H or —COCH$_3$; and its 16, 17, 18, 19 tetrahydroderivatives and 16, 17, 18, 19, 28, 29 hexahydroderivatives and corresponding oxidized products having the formula

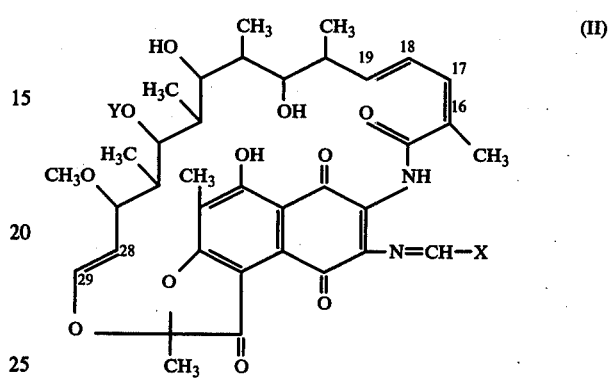

(II)

wherein X and Y are as above defined for formula (I) and is also concerned with their 16, 17, 18, 19 tetrahydroderivatives and 16, 17, 18, 19, 28, 29 hexahydroderivatives.

It is well known to those skilled in the art that upon reduction of rifamycin S and its derivatives substituted at position 3, such as 3-amino-rifamycin S of formula III, the corresponding rifamycins SV would be provided.

The compounds of formula (I) according to the present invention (which compounds are the Schiff bases for 3-amino-rifamycins) can be obtained by reacting an aldehyde of formula

X — CHO wherein X is as above defined, with 3-amino-rifamycin SV.

Similarly, from 16, 17, 18, 19 tetrahydroderivatives and 16, 17, 18, 19, 28, 29 hexahydroderivatives, and still by reaction with an aldehyde of the type as hereinabove shown, the 16, 17, 18, 19 tetrahydroderivatives and 16, 17, 18, 19, 28, 29 hexahydroderivatives of the compounds of formula (I) are obtained.

Of course, 3-amino-rifamycin SV or its desacetyl-derivative can be directly used as a starting product for obtaining the compound of formula (I), in which case it is only needed to carry out the reaction with said aldehyde, but in practice such a process would not be convenient because of such a product being readily oxidable in air.

All of the compounds of formula (I) according to the invention are of a reddish colour and have a very high antibiotic activity on gram-positive germs, gram-negative germs and Mycobacterium Tuberculosis.

In order that the present invention be more clearly understood, some unrestrictive exemplary embodiments of the invention will now be described.

EXAMPLE 1

8 g 3-amino-rifamycin S were dissolved in 25 ml acetic acid and 15 ml tetrahydrofuran. The solution was added with 1 g zinc and after 5 minutes a solution of 3 g 2-pyrrolaldehyde in 10 ml tetrahydrofuran was dropwise added thereto. The resulting solution was stirred at room temperature for 2 hours, the mixture was diluted with 200 ml dichloromethane, the undissolved zinc was filtered and the organic phase washed with an aqueous solution of bisodic phosphate and then with water. After drying on sodium sulphate, the product was filtered and concentrated to a small volume. By addition of petroleum ether, 3.5 g of a red product of formula I were precipitated, wherein X is 2-pyrryl and Y is —COCH$_3$. The electronic absorption spectrum in methanol shows a peak at 454 m$\mu$ (E$_{1cm}^{1\%}$ = 122).

EXAMPLE 2

8 g 3-amino-rifamycin S were dissolved in 15 ml tetrahydrofuran, reduced with 1 g zinc and 25 ml acetic acid and reacted with 3.4 g 2-thiophenaldehyde at 40° C. for 15 minutes. Stirring was continued for a few minutes at room temperature, then the red precipitate formed was filtered and washed with a mixture of acetic acid and tetrahydrofuran at a ratio 5:3. The precipitate was dissolved with 100 ml chloroform, the organic layer washed with an aqueous solution of bisodic phosphate and then with water. The chloroform layer was dried on sodium sulphate, the solvent evaporated, the product was diluted with 30 ml dichloromethane and precipitated with 100 ml petroleum ether. 5.4 g of a red product of formula I were yielded, wherein X is 2-thienyl and Y is —COCH$_3$. The electronic absorption spectrum in methanol shows a peak at 457 m$\mu$ (E$_{1cm}^{1\%}$ = 118).

By using tetramethylsilane as internal reference, the nuclear magnetic resonance spectrum shows the most significant peaks at $\delta$: 14.25(s); 13.07(s); 12.53(s); 10.20(s); 9.73(s); 7.0/7.6(m); 5.10(dd); 4.93(d); 3.05(s); 2.20(s); 2.10(s); 2.03(s); 1.81(s); 0.95(d); 0.56(d); 0.41(d) and -0.23(d) p.p.m.

EXAMPLE 3

A mixture of 8 g 3-amino-rifamycin S, 15 ml tetrahydrofuran, 3.5 g 2-flurorbenzaldehyde and 25 ml acetic acid was added with 1 g zinc and stirred at 15° C. for 10 minutes. The red abundant precipitate formed was filtered, washed with a mixture of acetic acid-tetrahydrofuran 5:3 and dissolved with 200 ml chloroform. The chloroform solution was washed with water, dried on sodium sulphate and concentrated to 50 ml. After crystallization in refrigerator, the product was filtered, thus obtaining 3.5 g of a red product of formula I, wherein X is 2-fluorophenyl and Y is —COCH$_3$. The electronic absorption spectrum in methanol shows a peak at 465 m$\mu$ (E$_{1cm}^{1\%}$ = 124).

EXAMPLE 4

8 g 3-amino-rifamycin S were dissolved in 30 ml dyglym, added with 4.5 g 2-fluoro-6-chlorobenzaldehyde and a solution of 2 g sodium ascorbate in 5 ml water. The solution was stirred at 40° C. for 15 minutes, then added with 30 ml chloroform and heated to 30° C. for 2 hours. The precipitate obtained was filtered, dissolved in 200 ml chloroform, maintained under stirring in air for 2 hours and the solution was then evaporated. The residue was crystallized from methanol. After filtering and drying, 3.8 g of a product of formula I were obtained, wherein X is 2-fluoro-6-chlorophenyl and Y is —COCH$_3$.

The electronic absorption spectrum in methanol shows a peak at 463 m$\mu$ (E$_{1cm}^{1\%}$ = 120.6).

By using tetramethylsilane as internal reference, the nuclear magnetic resonance spectrum in CDCL$_3$ shows the most significant peaks at $\delta$: 18.53(s); 15.85(s); 15.07(s); 10.20(s); 9.78(s); 6.70/7.45(m); 5.07(dd); 4.87(d); 3.01(s); 2.10(s); 2.02(s); 1.85(s); 0.91(d); 0.53(d); 0.17(d) and -0.32(d) p.p.m.

By the process described in this example, in addition to the above defined compound, chromatography on thin layer pointed out the formation of a different compound which is the subject of a copending patent application in the name of the same applicants.

EXAMPLE 5

8 g 3-amino-rifamycin S were dissolved in 30 ml dyglym and added with a solution of 2 g sodium ascorbate in 5 ml water.

After adding 4 g cinnamic aldehyde, the solution was stirred at 40° C. for 15 minutes, then added with 30 ml chloroform. Stirring was continued at 40° C. for 2 hours, and after addition of 300 ml chloroform the solution was washed with water. After drying, the solvent was evaporated. The residue was dissolved in 10 ml methanol, treated with an aqueous solution of sodium ascorbate and then poured into a solution of sodium metabisulphite. The solid precipitate was extracted with ethyl ether, the ether phase evaporated and the residue was dissolved with diisopropyl ether. 0.500 g of a product of formula I were obtained, wherein X is $\beta$-styryl and Y is —COCH$_3$. The electronic absorption spectrum in methanol shows a peak at 450 m$\mu$ (E$_{1cm}^{1\%}$ = 82.2).

Similarly, by reacting 3-amino-16, 17, 18, 19, 28, 29-hexahydro-25-desacetyl-rifamycin S, the 25-desacetyl-16, 17, 18, 19, 28, 29-hexahydroderivative of the product characterized in the above described example is obtained.

EXAMPLE 6

6.5 g of the product of formula I obtained in Example 2 were dissolved in 100 ml dichloromethane. 3 g manganese dioxide were added and the solution was stirred at room temperature for 75 minutes. The solution was filtered, the solvent evaporated, then adding petroleum ether and filtering again. By stove drying at 35° C., 5.5 g of a product of formula II were obtained, wherein X is 2-thienyl and Y is —COCH$_3$. The electronic absorption spectrum in methanol shows a peak at 530 m$\mu$.

EXAMPLE 7

A mixture of 8 g 3-amino-rifamycin S, 1.5 g zinc, and 5.2 g 1-phenyl-5-formyltetrazole was added with 15 ml tetrahydrofuran and 25 ml acetic acid. The solution was stirred at 0° C. for 4 hours, filtered, washed with a 3.5 mixture of tetrahydrofuran-acetic acid, the solid dissolved in ethyl ether, washed with water and then extracted with buffer phosphate at pH 7.5. The aqueous phase was acidified to pH 3.5 and then extracted again with chloroform. The organic layer was washed with water and dried. By solvent evaporation, 1.7 g of a product of formula I were obtained, wherein X is 1-phenyl-5-tetrazolyl and Y is —COCH$_3$.

The electronic absorption spectrum in methanol shows a peak at 452 m$\mu$ (E$_{1cm}^{1\%}$ = 72.2).

EXAMPLE 8

A mixture of 8 g 3-amino-rifamycin S, 1 g zinc and 6 g 1-phenyl-2,5-dimethyl-3-pyrrolaldehyde was added with 15 ml tetrahydrofuran and 25 ml acetic acid. The mixture was stirred at room temperature for 25 minutes, filtered and dropwise added to an aqueous solution of sodium sulphite. The mixture was filtered again and the solid dissolved in minimum volume of methyl alcohol, then diluting with 200 ml ethyl ether, washing with an aqueous solution of ascorbic acid and then with water. After drying and solvent evaporation, 2.7 g of a product of formula I were obtained, wherein X is 1-phenyl-2,5-dimethyl-3-pyrryl and Y is —COCH$_3$.

The electronic absorption spectrum in methanol shows a peak at 457 m$\mu$ ($E_{1cm}^{1\%} = 81.3$).

EXAMPLE 9

A mixture of 8 g 3-amino-rifamycin S, 1.5 g zinc and 3 ml 5-methyl-2-furanaldehyde was added with 15 ml tetrahydrofuran and 25 ml acetic acid. The mixture was cooled down to −20° C. and stirred at this temperature for 90 minutes. The reaction mixture was dissolved in 300 ml ethyl ether, filtered, washed with water, with an aqeuous solution of sodium metabisulphite, again with water and finally dried. The solution was concentrated to beginning of crystallization and filtered after one night in refrigerator. 8.8 g of a product of formula I were obtained, wherein X is 5-methyl-2-furyl and Y is —COCH$_3$.

The electronic absorption spectrum in methanol shows a peak at 456 m$\mu$ ($E_{1cm}^{1\%} = 99.7$).

EXAMPLE 10

A solution of 8 g 3-amino-rifamycin S in 30 ml dyglym was added with a solution of 2 g sodium ascorbate in 5 ml water and kept under stirring for 5 minutes. Then, 4 g 2-formylthianaphtene were added, heating to 40° C. for 15 minutes. The resulting solution was added with 30 ml chloroform and kept under stirring at 40° C. for further 60 minutes. The reaction mixture diluted with 200 ml chlorofrom was washed with water. After solvent evaporation, the residual oil was poured into an aqueous solution of sodium metabisulphite and the solid obtained was dissolved with 100 ml acetic acid of 50% titer. The crystalline solid obtained was thoroughly washed with water and dried, thus yielding 4.2 g of a product of formula I, wherein X is 2-thianaphtyl and Y is —COCH$_3$.

The electronic absorption spectrum in methanol shows a peak at 470 m$\mu$ ($E_{1cm}^{1\%} = 105.2$).

EXAMPLE 11

A solution of 8 g 3-amino-rifamycin S and 5 g 2-chloro benzaldehyde in 20 ml tetrahydrofuran was added with 1 g zinc and then cooled down to 0° C. The solution was added with 25 ml acetic acid and stirred at 0° C. for 160 minutes. The solid formed was filtered, washed with acetic acid and dissolved at 0° C. in 200 ml dichloromethane. The zinc was filtered, washed with water, dried and the solvent evaporated, thus yielding 4.6 g of a product of formula I, wherein X is 2-chlorophenyl and Y is —COCH$_3$.

The electronic absorption spectrum in methanol shows a peak at 470 m$\mu$ ($E_{1cm}^{1\%} = 115.7$).

EXAMPLE 12

A solution of 8 g 3-amino-rifamycin S in 20 ml tetrahydrofuran and 45 ml acetic acid was added with 3.1 ml 5,6-dihydro2H-3-pyranaldehyde and 2 g zinc. After stirring at room temperature for 5 hours and one night in refrigerator, the precipitate was filtered, dissolved in dichloromethane and washed with water. After anhydridation, the solvent was evaporated and the residue recrystallized from acetone, thus yielding 2 g of a product of formula I, wherein X is 3-[5,6-dihydro-2H-]-pyranyl and Y is —COCH$_3$. The electronic absorption spectrum in methanol shows a peak at 457 m$\mu$ ($E_{1cm}^{1\%} = 113.8$).

Similarly, by reacting 3-amino-16, 17, 18, 19, 28, 29-hexahydro-25-desacetyl-rifamycin S, the 25-desacetyl-16, 17, 18, 19, 28, 29-hexahydroderivative of the product characterized in the above described example is obtained.

What is claimed is:

1. A rifamycin compound having the formula

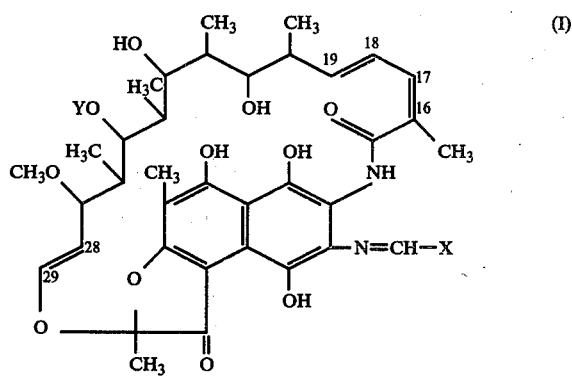

wherein: X is a radical selected from the group comprising aromatic hydrocarbon having from 6 to 8 C atoms; aromatic hydrocarbon-alkenyl having 8 C atoms; a heterocyclo selected from the group consisting of thiophene, furan and pyrrole; tetrazole; pyrane; a 5 or 6 member heterocycle condensed with an aromatic hydrocarbon having from 6 to 8 C atoms wherein the heterocycle has 1 or 2 hetero-atoms selected from the group consisting of O and S; substitution products of the above specified radicals having from 1 to 4 radicals differing therefrom and selected from the group consisting of halogen, hydroxyl, alkoxyl having less than 7 C atoms, nitro, amino, N-alkylamino having less than 3 C atoms, N,N-dialkylamino having from 2 to 4 C atoms, carboxyl, carboalkoxy having from 2 to 5 C atoms, carboxyalkoxy having 2 or 3 C atoms, dialkylaminoalkoxy having from 3 to 6 C atoms, acetoxy, acetamido; Y is —H or —COCH$_3$; and its 16, 17, 18, 19 tetrahydroderivatives and 16, 17, 18, 19, 28, 29 hexahydroderivatives and corresponding oxidized products having the formula

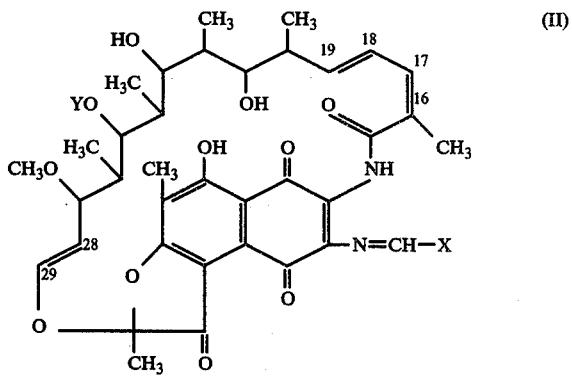

* * * * *